(12) United States Patent
Tarumi et al.

(10) Patent No.: US 12,423,600 B2
(45) Date of Patent: Sep. 23, 2025

(54) INTEGRATION DEVICE, INTEGRATION METHOD, AND STORAGE MEDIUM

(71) Applicant: Hitachi, Ltd., Tokyo (JP)

(72) Inventors: Shinji Tarumi, Tokyo (JP); Wataru Takeuchi, Tokyo (JP); Shuntaro Yui, Tokyo (JP); Hideyuki Ban, Tokyo (JP)

(73) Assignee: HITACHI, LTD., Tokyo (JP)

( * ) Notice: Subject to any disclaimer, the term of this patent is extended or adjusted under 35 U.S.C. 154(b) by 994 days.

(21) Appl. No.: 17/496,178

(22) Filed: Oct. 7, 2021

(65) Prior Publication Data

US 2022/0138603 A1  May 5, 2022

(30) Foreign Application Priority Data

Nov. 4, 2020 (JP) .................. 2020-184257

(51) Int. Cl.
*G06N 5/04* (2023.01)
*G06N 20/00* (2019.01)

(52) U.S. Cl.
CPC ............. *G06N 5/041* (2013.01); *G06N 20/00* (2019.01)

(58) Field of Classification Search
None
See application file for complete search history.

(56) References Cited

U.S. PATENT DOCUMENTS 6,223,164 B1 * 4/2001 Seare .................. G16H 40/20
 705/2
8,131,783 B2 * 3/2012 Matsuzawa ......... G06F 12/0223
 707/822
9,600,389 B2 * 3/2017 Filho .................... G06F 11/302
9,601,010 B2 * 3/2017 Itaya ..................... G06F 30/00
2004/0111433 A1 * 6/2004 Seto ..................... G16H 50/70

(Continued)

FOREIGN PATENT DOCUMENTS

JP 2015-158935 A 9/2015
JP 2018-005317 A 1/2018

(Continued)

OTHER PUBLICATIONS

Japanese Office Action issued on Oct. 24, 2023 for Japanese Patent Application No. 2020-184257.

*Primary Examiner* — Maikhanh Nguyen
(74) *Attorney, Agent, or Firm* — Volpe Koenig

(57) ABSTRACT

Provided is an integration device that is accessible to statistical information based on analysis target data of each of a plurality of analysis target devices and includes a processor configured to execute a program and a storage device configured to store the program. The integration device executes acquisition processing of acquiring first statistical information and second statistical information from a plurality of pieces of statistical information, integration processing of integrating the first statistical information and the second statistical information acquired by the acquisition processing by statistical processing based on the number of first data of first analysis target data used for statistical processing of the first statistical information and the number of second data of second analysis target data used for statistical processing of the second statistical information, and output processing of outputting integration statistical information obtained by the integration processing.

11 Claims, 11 Drawing Sheets

(56) References Cited

U.S. PATENT DOCUMENTS

| | | | |
|---|---|---|---|
| 2013/0317847 A1* | 11/2013 | Yui | G16H 70/60 |
| | | | 705/2 |
| 2015/0212873 A1* | 7/2015 | Filho | G06F 11/3068 |
| | | | 707/688 |
| 2015/0320362 A1* | 11/2015 | Hasegawa | A61B 5/08 |
| | | | 600/529 |
| 2016/0246981 A1 | 8/2016 | Nakagawa et al. | |
| 2017/0042495 A1* | 2/2017 | Matsuzaki | A61B 5/055 |
| 2018/0018590 A1 | 1/2018 | Szeto et al. | |
| 2020/0250579 A1* | 8/2020 | Takeuchi | G06N 5/01 |
| 2021/0117863 A1* | 4/2021 | Soleimani | G06N 5/045 |

FOREIGN PATENT DOCUMENTS

| | | |
|---|---|---|
| JP | 2019-526851 A | 9/2019 |
| WO | 2019/220486 A1 | 11/2019 |

* cited by examiner

INTEGRATION DEVICE, INTEGRATION METHOD, AND STORAGE MEDIUM

CLAIM OF PRIORITY

The present application claims priority from Japanese patent application JP 2020-184257 filed on Nov. 4, 2020, the content of which is hereby incorporated by reference into this application.

BACKGROUND OF THE INVENTION

1. Field of the Invention

The present invention relates to an integration device, an integration method, and an integration program for integrating data.

2. Description of the Related Art

With a progress of computerization of health care information, attention has been focused on utilization of health care data held by a local government or a medical institution. In particular, by utilizing data of a plurality of organizations in a traverse manner, it is expected that highly reliable analysis such as service quality evaluation backed for a large number of samples can be performed. However, the health care data is sensitive data, and it is not easy to disclose or take out the health care data to an outside of the organization that manages the health care data from a viewpoint of personal information protection and logic. Therefore, as a technique for solving these problems, a technique of directly analyzing the data without taking out the data to the outside has been developed.

A data-hidden statistical processing system of JP-A-2015-158935 (Patent Literature 1) includes a plurality of data input devices each including a unit configured to acquire original data to be hidden and a unit configured to divide original data Xi into partial data X1$i$ and X2$i$ in accordance with a secret ratio such that the original data Xi is restored when all the partial data are added up and output the partial data X1$i$ and X2$i$. Each of cloud services performs a predetermined calculation using, as input data, either the partial data X1$i$ or X2$i$ output from each of the plurality of data input devices and outputs a calculation result. A statistical processing result providing service obtains and provides a result of statistical processing based on a plurality of original data Xi acquired by the plurality of data input devices by using the calculation result output from each of the cloud services.

A distributed online machine learning system of JP-T-2019-526851 (Patent Literature 2) includes plural private data servers each having local private data. A researcher can request a related private data server to train implementation of a machine learning algorithm with the local private data without requesting anonymization of the private data or exposing the private data to an unpermitted computing system. Further, the private data server generates synthesized data or proxy data according to data distribution of actual data. The server trains a proxy model using the proxy data. When the proxy model is sufficiently similar to a trained real model, the proxy data, a proxy model parameter, or other learned knowledge can be transmitted to one or a plurality of non-private calculation devices. Knowledge learned from the plural private data servers can be aggregated into one or more trained global models without disclosing the private data.

A medical data processing device of JP-A-2018-005317 (Patent Literature 3) includes a reception unit that receives, from a terminal of a first medical institution, intermediate data that is generated by processing a plurality of medical data using a specific algorithm and is not restored to any of the plurality of medical data, a storage processing unit that stores the received intermediate data in a storage device, and a transmission unit that transmits the intermediate data read from the storage device to a terminal of a second medical institution.

However, in the data-hidden statistical processing system of Patent Literature 1, it is necessary to take out a part of a record of the original data to the outside of the organization. Further, when there are a plurality of data, the data-hidden statistical processing system cannot construct an integration model of any combination.

In the distributed online machine learning system of Patent Literature 2, when an integration model is constructed, since pseudo data collected from each data set is used, a model that is exactly the same as that when the data is actually integrated cannot be constructed.

The medical data processing device of Patent Literature 3 is limited to taking out a result of statistical processing, and cannot construct entire statistical information or a model that can be constructed based on the entire statistical information when a plurality of data are integrated.

SUMMARY OF THE INVENTION

An object of the invention is to generate statistical data of an analysis target group without taking out analysis target data held by each analysis target to an outside of the analysis target.

An integration device according to an aspect of the invention disclosed in the present application is accessible to statistical information based on analysis target data of each of a plurality of analysis target devices and includes a processor configured to execute a program and a storage device configured to store the program. The processor is configured to execute acquisition processing of acquiring first statistical information and second statistical information from a plurality of pieces of statistical information, integration processing of integrating the first statistical information and the second statistical information acquired by the acquisition processing by statistical processing based on the number of first data of first analysis target data used for statistical processing of the first statistical information and the number of second data of second analysis target data used for statistical processing of the second statistical information, and output processing of outputting integration statistical information obtained by the integration processing.

According to a representative embodiment of the invention, statistical data of an analysis target group can be generated without taking out analysis target data held by each analysis target to an outside of the analysis target. Problems, configurations, and effects other than those described above will become apparent from the following description of embodiments.

DESCRIPTION OF THE PREFERRED EMBODIMENTS

An integration device according to the present embodiment constructs an integration model having no information loss in any combination without taking out or integrating sensitive analysis target data managed by each of a plurality of analysis targets. Hereinafter, a detailed description will be given with reference to the accompanying drawings.

<System Configuration Example of Integration Analysis System>

Figure 1:
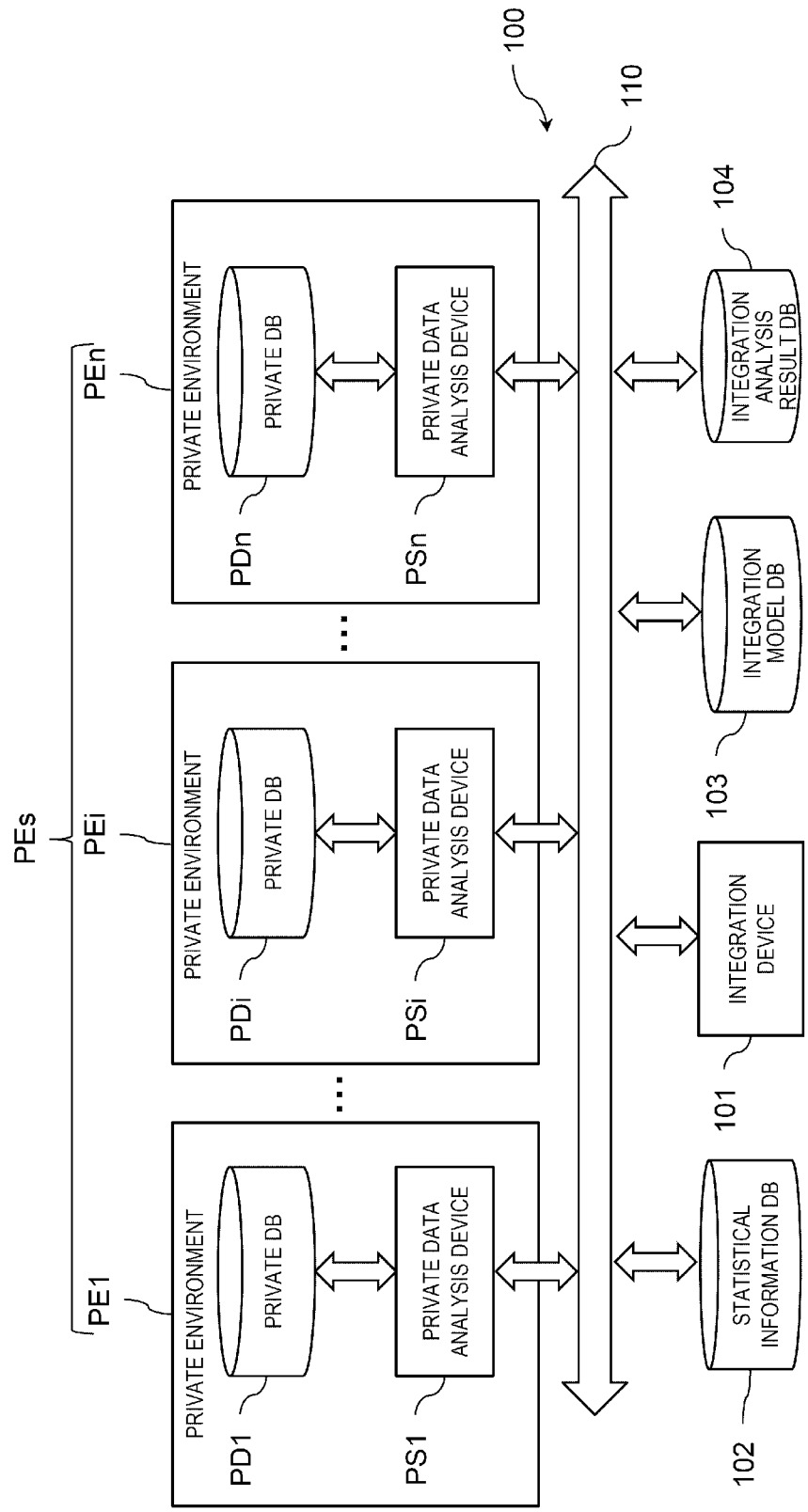
FIG. 1 is a block diagram showing a system configuration example of an integration analysis system.

FIG. 1 is a block diagram showing a system configuration example of an integration analysis system. An integration analysis system 100 includes a private environment group PEs, an integration device 101, a statistical information DB (database) 102, an integration model DB 103, and an integration analysis result DB 104. These elements are communicably connected via a network 110 such as the Internet, a local area network (LAN), or a wide area network (WAN).

The private environment group PEs includes a plurality of private environments PEi to PEn (i is an integer satisfying 1≤i≤n, and n is an integer equal to or greater than 2). The private environment PEi is an environment computerized by a business operator such as a company in addition to a local government or a medical institution, and includes a private data analysis device PSi and a private DB PDi to be analyzed.

The private data analysis device PSi is a computer that analyzes private data that is analysis target data, calculates statistical information, and transmits the statistical information to the statistical information DB 102 or the integration device 101. The private DB PDi is a database that stores the private data. The private data is data that is not allowed to leak to an outside of the private DB PDi in terms of protection of personal information or security. Specifically, for example, the private data is numerical data that can be statistically processed, such as personal data (age, income, and the like), electronic medical records (body length, weight, blood glucose level, uric acid value, and the like), and accounting data (sales, profit, and the like).

The private environment group PEs is a set of the private environments PEi of the same type in order to statistically process the private data of each private environment PEi. For example, in a case of an integration analysis system for the medical institution, the private environment group PEs is a set of private environments PEi of the medical institution.

The integration device 101 is a computer that integrates the statistical information of each private environment PEi stored in the statistical information DB 102, generates an integration model, and verifies the integration model. The integration device 101 can access data in the statistical information DB 102, the integration model DB 103, and the integration analysis result DB 104, and cannot access the private data in the private DB PDi.

The statistical information DB 102 is a database that stores the statistical information from each private data analysis device PSi. The integration model DB 103 is a database that stores the integration model or an integration model parameter applied to the integration model. The integration analysis result DB 104 is a database that stores integration statistical information obtained by integrating the statistical information of each private environment PEi, and a verification result of the integration model parameter.

<Hardware Configuration Example of Computer (Integration Device 101, Private Data Analysis Device PSi)

Figure 2:
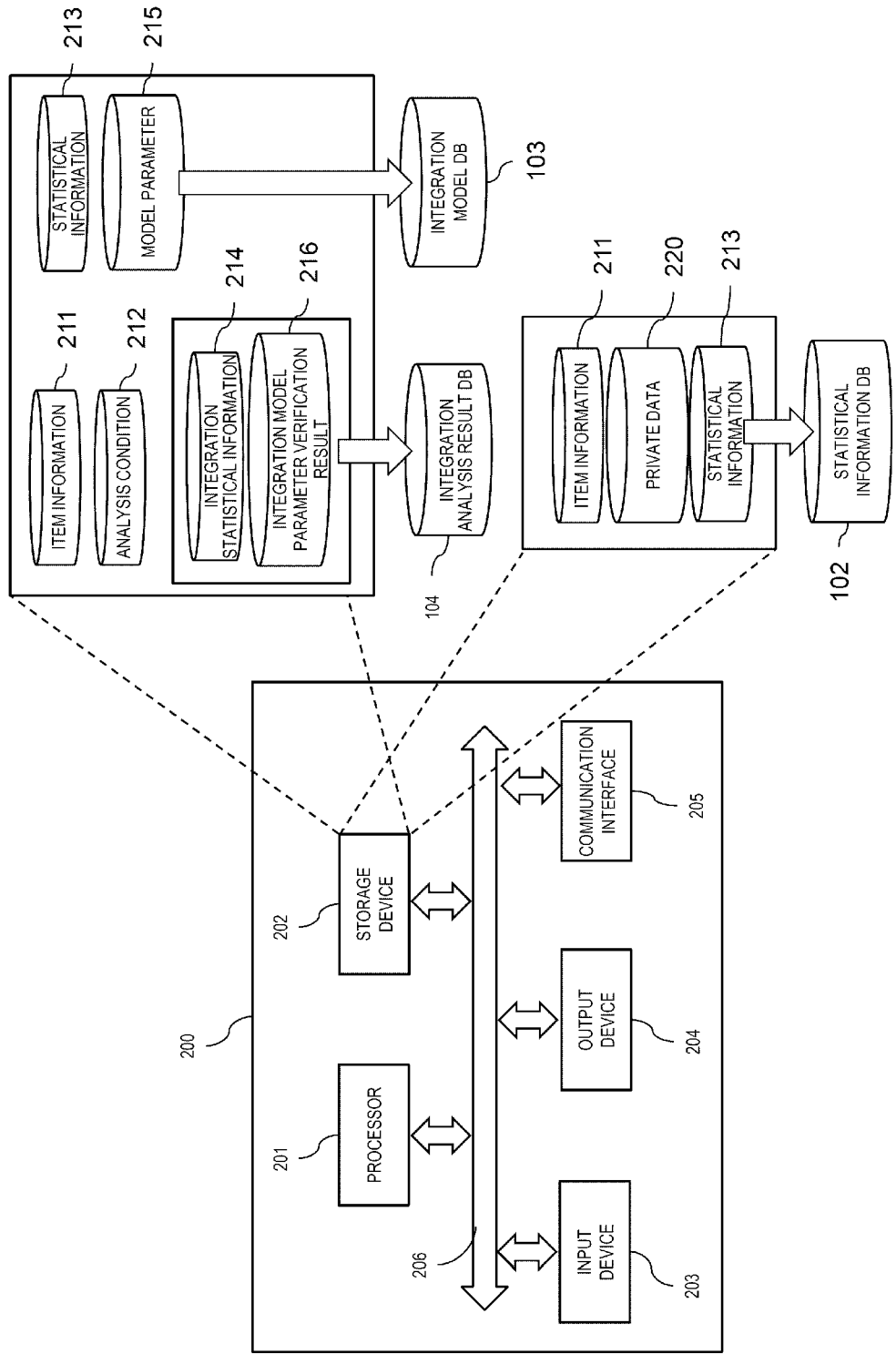
FIG. 2 is a block diagram showing a hardware configuration example of a computer.

FIG. 2 is a block diagram showing a hardware configuration example of a computer. A computer 200 includes a processor 201, a storage device 202, an input device 203, an output device 204, and a communication interface (communication IF) 205. The processor 201, the storage device 202, the input device 203, the output device 204, and the communication IF 205 are connected by a bus 206. The processor 201 controls the computer 200. The storage device 202 serves as a work area of the processor 201. Further, the storage device 202 is a non-transitory or temporary recording medium that stores various programs and data. Examples of the storage device 202 include a read only memory (ROM), a random access memory (RAM), a hard disk drive (HDD), and a flash memory. The input device 203 inputs data. Examples of the input device 203 include a keyboard, a mouse, a touch panel, a numeric keypad, a scanner, and a microphone. The output device 204 outputs data. Examples of the output device 204 include a display, a printer, and a speaker. The communication IF 205 is connected to the network 110 and transmits and receives data.

When the computer 200 is the integration device 101, the storage device 202 stores item information 211, an analysis condition 212, statistical information 213, integration statistical information 214, a model parameter 215, and an integration model parameter verification result 216.

The item information 211 is information indicating an item of private data 220 desired to be acquired by the integration device 101 as the statistical information, and does not include numerical data of the item. When the private data 220 is the electronic medical record, the item information 211 is information indicating items such as a body length, a weight, a blood glucose level, and a uric acid level, and does not include numerical data of the body length, the weight, the blood glucose level, or the uric acid level.

The analysis condition 212 is a condition for the integration device 101 to analyze the statistical information 213. Specifically, for example, the analysis condition 212 includes variable information indicating what an objective variable is and which explanatory variable an item is, and identification information for specifying an integration source indicating the statistical information 213 of which private environment PEi is integrated. Details of the analysis condition 212 will be described later with reference to FIG. 4.

The statistical information 213 is data obtained by statistically processing the private data 220 by the private data analysis device PSi. Specifically, for example, the statistical information 213 includes an average value, a sum of square of deviation, and a sum of product of deviation of the private data 220. Details of the statistical information 213 will be described later with reference to FIG. 3.

The integration statistical information 214 is an integration result obtained by integrating a plurality of pieces of statistical information, and is also stored in the integration analysis result DB 104. The model parameter 215 is a parameter set in the integration model, and is also stored in the integration model DB 103. The integration model parameter verification result 216 is data indicating a result of the verification of the model parameter 215 by the integration device 101, and is also stored in the integration analysis result DB 104.

Further, when the computer 200 is the private data analysis device PSi, the storage device 202 includes the item information 211, the private data 220, and the statistical information 213. As described above, the private data 220 is numerical data that can be statistically processed, such as the personal data, the electronic medical record, and the accounting data.

<Statistical Information>

Figure 3:
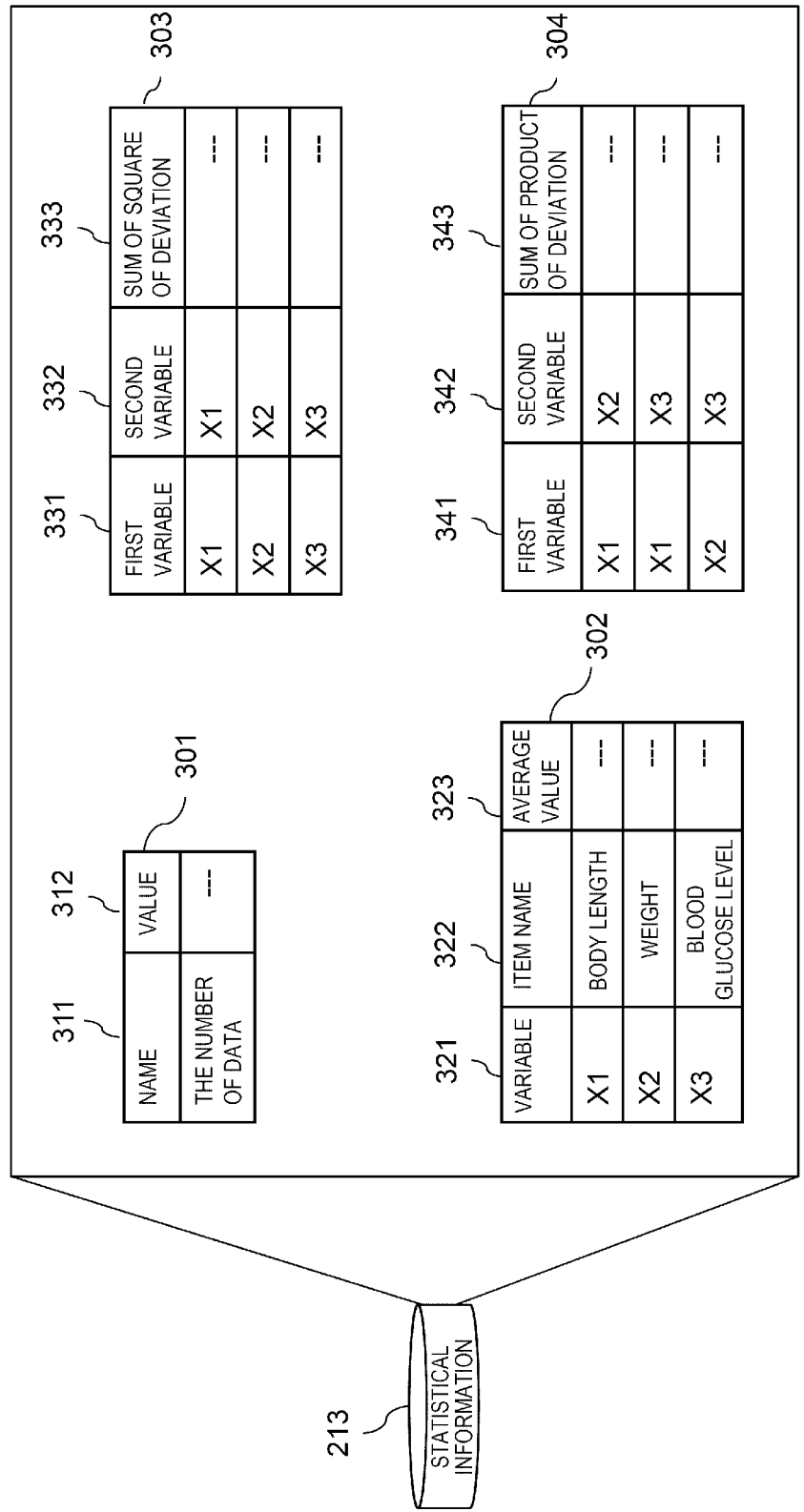
FIG. 3 is a diagram showing an example of statistical information.

FIG. 3 is a diagram showing an example of the statistical information. The statistical information 213 includes, for example, basic information 301, average value information 302, sum of square of deviation information 303, and sum of product of deviation information 304. The basic information 301 is a combination of a name 311 and a value 312. The name 311 defines an item indicating "the number of data" that is the basic information 301 as a value. The number of data means the number of pieces of data handled as the statistical information 213. In an example of the electronic medical record, the name 311 is an item of the number of electronic medical records, that is, the number of patients. The value 312 is numerical data of the item defined by the name 311. In the example of the electronic medical record, the value 312 is numerical data indicating the number of electronic medical records, that is, the number of patients.

The average value information 302 is a combination of a variable 321, an item name 322, and an average value 323. The variable 321 is a variable indicating an item specified by the item information. The item name 322 is a name for specifying the variable 321. In the example of the electronic medical record, for example, X1 is the body length, X2 is the weight, and X3 is the blood glucose level. The average value 323 is a numerical value obtained by averaging values (private data) of the variable 321.

The sum of square of deviation information 303 is a combination of a first variable 331, a second variable 332, and a sum of square of deviation 333. The first variable 331 and the second variable 332 are the same variable. The sum of square of deviation 333 is a sum of squared deviations. That is, the sum of square of deviation 333 is a sum obtained by obtaining, for each record of the private data 220 defining a value of the first variable 331, a value obtained by multiplying a deviation obtained by subtracting an average value of the first variable 331 from the value of the first variable 331 and a deviation obtained by subtracting an average value of the second variable 332 (the same value as the average value of the first variable 331) from a value of the second variable 332 (the same value as the value of the first variable 331), and adding values obtained by the above-described multiplication.

The sum of product of deviation information 304 is a combination of a first variable 341, a second variable 342, and a sum of product of deviation 343. The first variable 341 and the second variable 342 are different variables. The sum of product of deviation 343 is a product sum of the deviations. That is, the sum of product of deviation 343 is a sum obtained by obtaining, for each record of the private data 220 defining a combination of a value of the first variable 341 and a value of the second variable 342, a value obtained by multiplying a deviation obtained by subtracting an average value of the first variable 341 from the value of the first variable 341 and a deviation obtained by subtracting an average value of the second variable 342 from the value of the second variable 342 and adding values obtained by the above-described multiplication.

<Analysis Condition>

Figure 4:
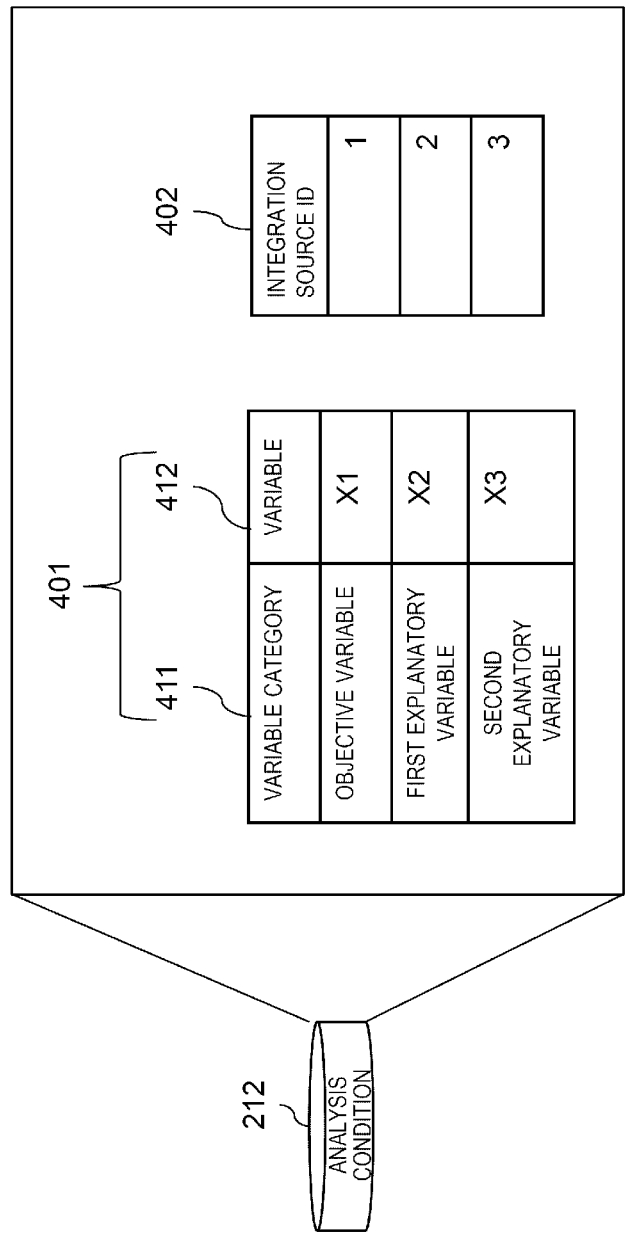
FIG. 4 is a diagram showing an example of an analysis condition.

FIG. 4 is a diagram showing an example of the analysis condition 212. The analysis condition 212 includes a variable information table 401 and an integration source information table 402. The variable information table 401 has information for defining a variable used in the integration model, and includes a variable category 411 and a variable 412. The variable category 411 defines a type of the variable 412 (objective variable, first explanatory variable, and second explanatory variable). The variable 412 defines the variable to be applied to the variable category 411. In FIG. 4, a variable X1 is defined as the objective variable, a variable X2 is defined as the first explanatory variable, and a variable X3 is defined as the second explanatory variable.

The integration source information table 402 includes an integration source ID. The integration source ID is identification information i for uniquely specifying the private environment PEi having the statistical information 213 to be integrated. Accordingly, the integration device 101 integrates three pieces of statistical information from the private environments PE1, PE2, and PE3 in which the objective variable is X1, the first explanatory variable is X2, the second explanatory variable is X3, and the integration source IDs are i=1, 2, and 3, respectively.

<Statistical Information Calculation Processing>

Figure 5:
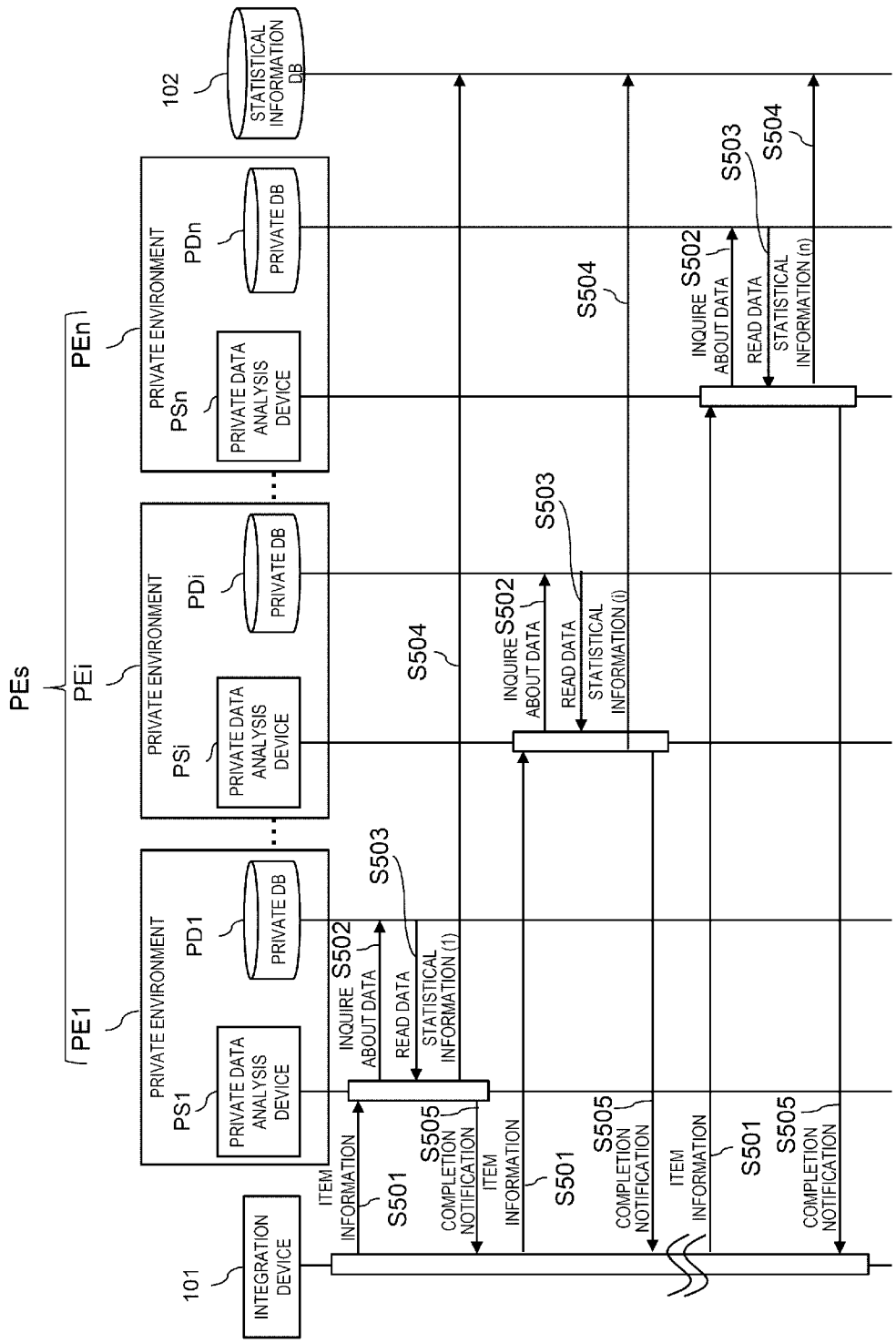
FIG. 5 is a sequence diagram showing an example of statistical information calculation processing.

FIG. 5 is a sequence diagram showing an example of statistical information calculation processing. The integration device 101 transmits the item information to the private data analysis device PSi at a predetermined timing (step S501).

When the private data analysis device PSi receives the item information, the private data analysis device PSi inquires of the private DB PDi about the private data 220 that is the value of the item of the item information (step S502), and reads the private data 220 from the private DB PDi (step S503). Then, the private data analysis device PSi statistically processes the read private data 220 to calculate the statistical information 213 (basic information 301, average value information 302, sum of square of deviation information 303, and sum of product of deviation information 304), and transmits the statistical information 213 to the statistical information DB 102 (step S504). When the transmission is completed, the private data analysis device PSi transmits a completion notification to the integration device 101 (step S505). In this way, the statistical information 213 is stored in the statistical information DB 102.

<Integration Model Construction Processing>

Figure 6:
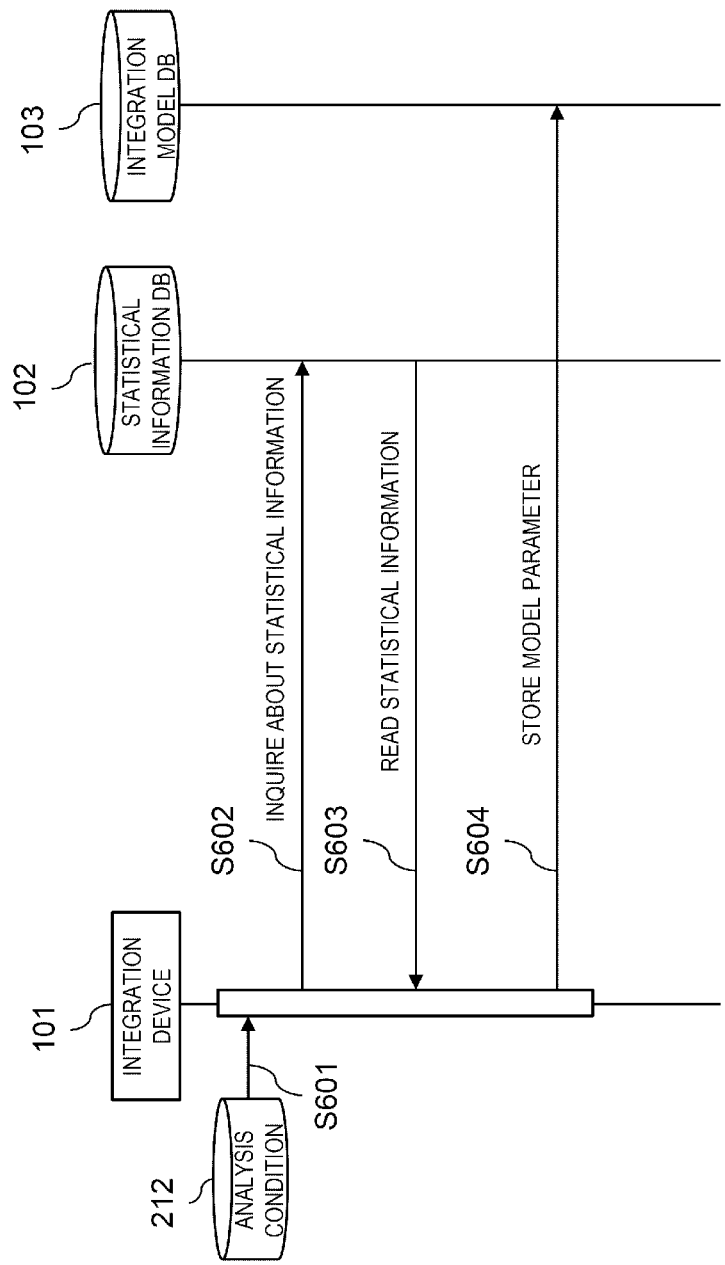
FIG. 6 is a sequence diagram showing an example of integration model construction processing performed by an integration device.

FIG. 6 is a sequence diagram showing an example of integration model construction processing by the integration device 101. When the integration device 101 acquires the analysis condition 212 (step S212), the integration device 101 inquires about the statistical information 213 of the private data analysis device PSi specified by the integration source information table 402 (step S602) and reads the statistical information 213 (step S603). Then, the integration device 101 generates the integration model and stores the integration model parameter in the integration model DB (step S604). In this way, the integration model parameter is stored in the integration model DB.

Figure 7:
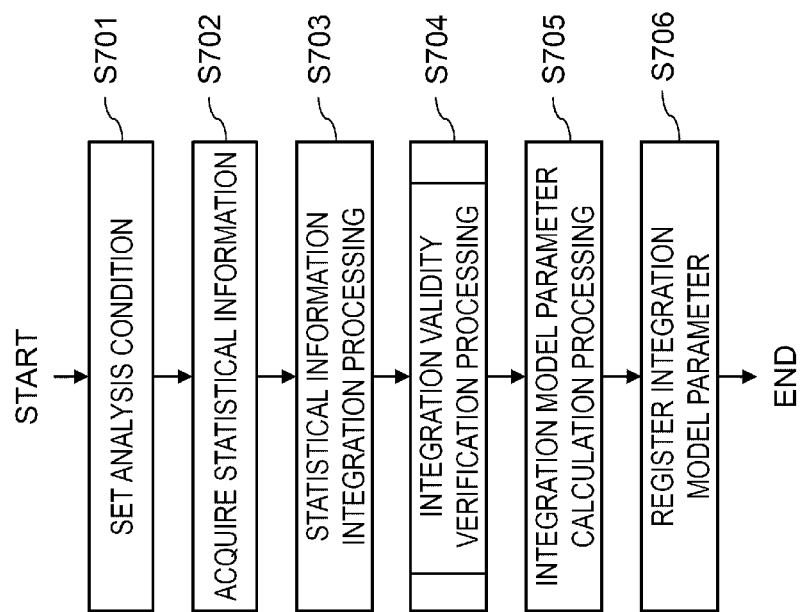
FIG. 7 is a flowchart showing an example of the integration model construction processing by the integration device.

FIG. 7 is a flowchart showing an example of the integration model construction processing by the integration device 101. The integration device 101 sets, for example, the analysis condition 212 by a user operation (step S701). Next, as shown in FIG. 6, the integration device 101 acquires the statistical information 213 to be integrated from the statistical information DB 102 (step S702).

Next, the integration device 101 executes the statistical information integration processing (step S703). Accordingly, the integration statistical information is calculated. In the statistical information integration processing (step S703), for example, the integration device 101 comprehensively selects and integrates two pieces of statistical information. For example, the integration device 101 attempts to integrate "statistical information 1" and "statistical information 2". The integration device 101 attempts to integrate "integration statistical information 1+2" (an integration result of the "statistical information 1" and the "statistical information 2") and "statistical information 3". Further, the integration device 101 attempts to integrate the "integration statistical information 1+2" (the integration result of the "statistical information 1" and the "statistical information 2") and "statistical information 3+4" (an integration result of the "statistical information 3" and "statistical information 4"). A specific example of the statistical information integration processing (step S703) will be described later with reference to FIGS. 8 and 9.

Next, the integration device 101 executes integration validity verification processing (step S704). The integration validity verification processing (step S704) is processing of verifying validity of the integration in the statistical information integration processing (step S703). Details of the integration validity verification processing (step S704) will be described later with reference to FIG. 10.

Thereafter, the integration device 101 executes integration model parameter calculation processing on the integration statistical information determined to be valid by the integration validity verification processing (step S704) to calculate the model parameter 215 (step S705). Specifically, for example, the integration device 101 inputs the integration statistical information 214 to a regression equation and calculates the model parameter 215 in the regression equation. Then, as shown in FIG. 6, the integration device 101 registers the calculated model parameter 215 in the integration model DB 103 (step S706). The integration device 101 may transmit the calculated model parameter 215 to the private data analysis device PSi. In this way, the integration model (regression equation in which the model parameter 215 is set) is constructed.

<Statistical Information Integration Processing (Step S703)

Figure 8:
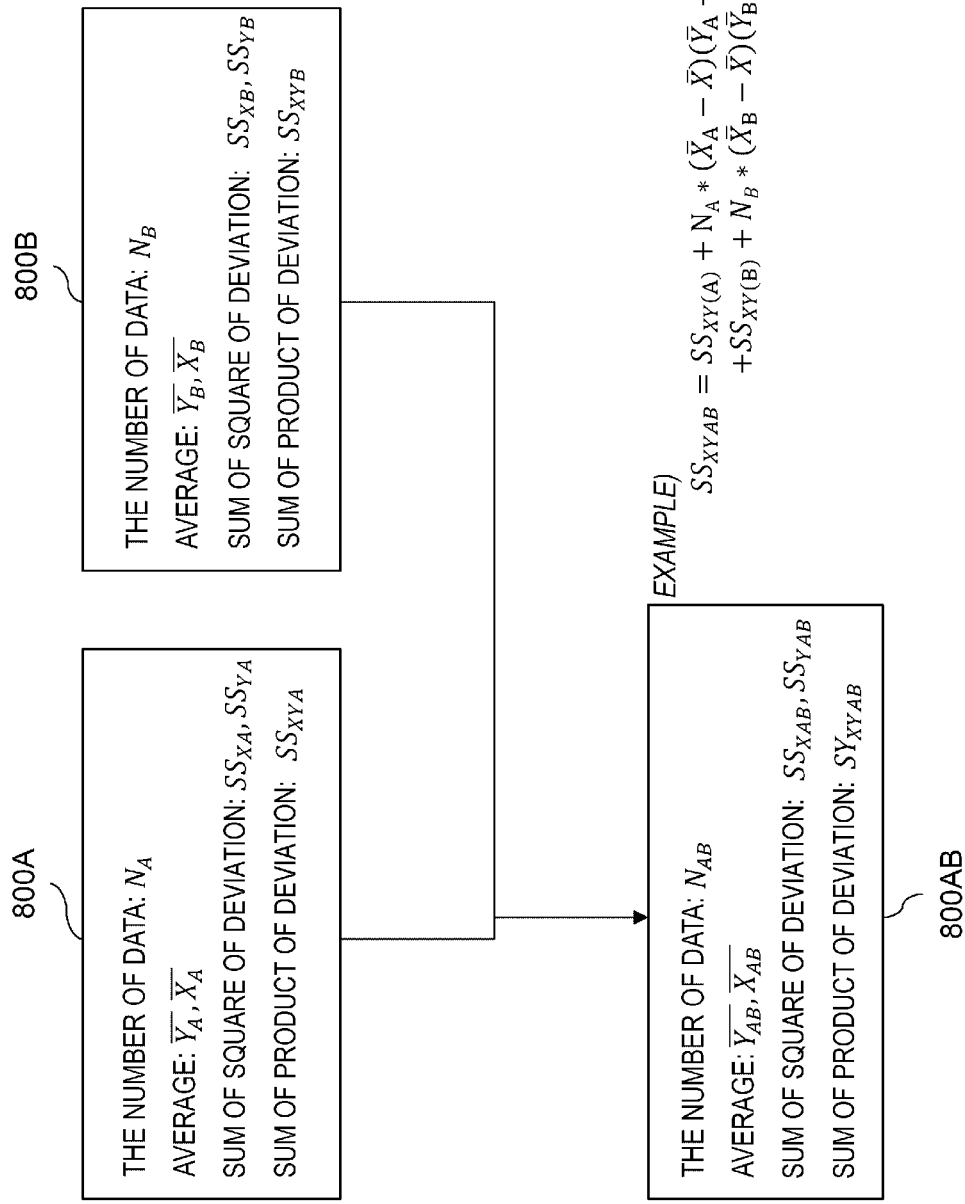
FIG. 8 is a diagram showing an example of statistical information integration processing (step S703).

FIG. 8 is a diagram showing an example of the statistical information integration processing (step S703). FIG. 8 shows the statistical information integration processing (step S703) for integrating two pieces of statistical information 213 (800A and 800B) in a case of single regression. Statistical values (the number of data, an average, a sum of square of deviation, and a sum of product of deviation) of the statistical information 800A and 800B are as shown in FIG. 8. In the statistical information 800A and 800B, X represents the explanatory variable, and Y represents the objective variable. A statistical value to which a suffix A is added indicates the statistical value included in the statistical information 800A, and a statistical value to which a suffix B is added indicates the statistical value included in the statistical information 800B.

Integration statistical information 800AB is an integration result obtained by integrating the statistical information 800A and the statistical information 800B. A statistical value to which a suffix AB is added indicates an integration statistical value obtained by integrating the statistical value of the statistical information 800A and the statistical value of the statistical information 800B.

Specifically, for example, the number of data NAB is a sum of the number of data $N_A$ and the number of data $N_B$, which are the values 312 of the number of data 311. In a case of the statistical information 800A, for example, $N_A$ pieces of data of $(X_{A1}, Y_{A1}), (X_{A2}, Y_{A2}), \ldots, (X_{ANA}, Y_{ANA})$ are included as the private data 220. Similarly, in a case of the statistical information 800B, for example, $N_B$ pieces of data of $(X_{B1}, Y_{B1}), (X_{B2}, Y_{B2}), \ldots, (X_{BNB}, Y_{BNB})$ are included as the private data 220. An average value of $X_{AB}$ is an integration average value obtained by integrating an average value of $X_A$ indicated as the average of the statistical information 800A and an average value of $X_B$ indicated as the average of the statistical information 800B based on the number of data $N_{AB}$, and is expressed by the following equation (1).

$$\overline{X_{AB}} = (\overline{X_A} * N_A + \overline{X_B} * N_B)/(N_A + N_B) \quad (1)$$

An average value of $Y_{AB}$ is an integration average value obtained by integrating an average value of $Y_A$ indicated as the average of the statistical information 800A and an average value of $Y_B$ indicated as the average of the statistical information 800B based on the number of data $N_{AB}$, and is expressed by the following equation (2).

$$\overline{Y_{AB}} = (\overline{Y_A} * N_A + \overline{Y_B} * N_B)/(N_A + N_B) \quad (2)$$

A sum of square of deviation $SS_{XAB}$ is an integration sum of square of deviation obtained by integrating a sum of square of deviation $SS_{XA}$ and a sum of square of deviation $SS_{XB}$ based on the integration average value of the equation (1), and is expressed by the following equation (3).

$$SS_{XAB} = SS_{XA} + N_A*(\overline{X_A} - \overline{X_{AB}})^2 + SS_{XB} + N_B*(\overline{X_B} - \overline{X_{AB}})^2 \quad (3)$$

A sum of square of deviation $SS_{YAB}$ is an integration sum of square of deviation obtained by integrating a sum of square of deviation $SS_{YA}$ and a sum of square of deviation $SS_{YB}$ based on the integration average value of the equation (2), and is expressed by the following equation (4).

$$SS_{YAB} = SS_{YA} + N_A*(\overline{Y_A} - \overline{Y_{AB}})^2 + SS_{YB} + N_B*(\overline{Y_B} - \overline{Y_{AB}})^2 \quad (4)$$

A sum of product of deviation $SS_{XYAB}$ is an integration sum of product of deviation obtained by integrating a sum of product of deviation $SS_{XYA}$ and a sum of product of deviation $SS_{XYB}$ based on the integration average values of the equations (1) and (2), and is expressed by the following equation (5).

$$SS_{XYAB} = SS_{XYA} + N_A*(\overline{X_A} - \overline{X_{AB}})(\overline{Y_A} - \overline{Y_{AB}}) + SS_{XYB} + N_B*(\overline{X_B} - \overline{X_{AB}})(\overline{Y_B} - \overline{Y_{AB}}) \quad (5)$$

Figure 9:
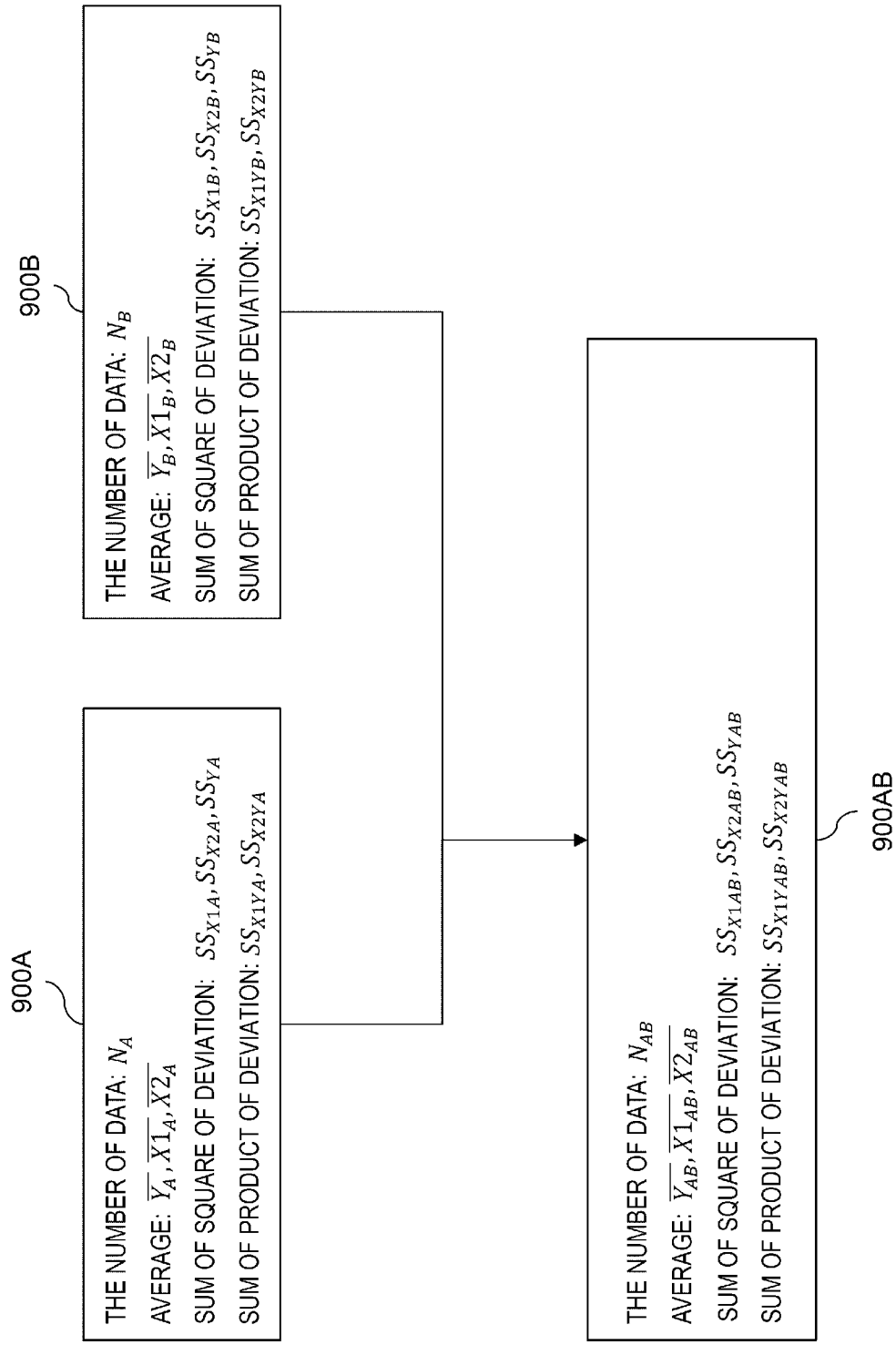
FIG. 9 is a diagram showing another example of the statistical information integration processing (step S703).

FIG. 9 is a diagram showing another example of the statistical information integration processing (step S703). FIG. 9 shows the statistical information integration processing (step S703) for integrating two pieces of statistical information 213 (900A and 900B) in a case of multiple regression. Statistical values (the number of data, an average, a sum of square of deviation, and a sum of product of deviation) of the statistical information 900A and 900B are as shown in FIG. 9. In the statistical information 900A and 900B, X1 and X2 indicate the explanatory variables, and Y indicates the objective variable. A statistical value to which the suffix A is added indicates the statistical value included in the statistical information 900A, and a statistical value to which the suffix B is added indicates the statistical value included in the statistical information 900B.

In a case of the statistical information 900A, for example, $N_A$ pieces of data of $(X1_{A1}, X2_{A1}, Y_{A1})$, $(X1_{A2}, X2_{A2}, Y_{A2})$, ..., $(X1_{ANA}, X2_{ANA}, Y_{ANA})$ are included as the private data 220. Similarly, in a case of the statistical information 900B, for example, $N_B$ pieces of data of $(X1_{B1}, X2_{B1}, Y_{B1})$, $(X1_{B2}, X2_{B2}, Y_{B2})$, ..., $(X1_{BNB}, X2_{BNB}, Y_{BNB})$ are included as the private data 220.

Integration statistical information 900AB is an integration result obtained by integrating the statistical information 900A and the statistical information 900B. A statistical value to which the suffix AB is added indicates an integration statistical value obtained by integrating the statistical value of the statistical information 900A and the statistical value of the statistical information 900B.

Specifically, for example, an average value of $X1_{AB}$ is an integration average value obtained by integrating an average value of $X1_A$ indicated as the average of the statistical information 900A and an average value of $X1_B$ indicated as the average of the statistical information 900B based on the number of data $N_{AB}$, and is expressed by the following equation (6).

$$\overline{X1_{AB}} = (\overline{X1_A}*N_A + \overline{X1_B}*N_B)/(N_A+N_B) \quad (6)$$

An average value of $X2_{AB}$ is an integration average value obtained by integrating an average value of $X2_A$ indicated as the average of the statistical information 900A and an average value of $X2_B$ indicated as the average of the statistical information 900B based on the number of data $N_{AB}$, and is expressed by the following equation (7).

$$\overline{X2_{AB}} = (\overline{X2_A}*N_A + \overline{X2_B}*N_B)/(N_A+N_B) \quad (7)$$

An average value of $Y_{AB}$ is an integration average value obtained by integrating an average value of $Y_A$ indicated as the average of the statistical information 900A and an average value of $Y_B$ indicated as the average of the statistical information 900B based on the number of data $N_{AB}$, and is expressed by the equation (2).

A sum of square of deviation $SS_{X1AB}$ is an integration sum of square of deviation obtained by integrating a sum of square of deviation $SS_{X1A}$ and a sum of square of deviation $SS_{X1B}$ based on the integration average value of the equation (6), and is expressed by the following equation (8).

$$SS_{X1AB} = SS_{X1A} + N_A*(\overline{X1_A}-\overline{X1_{AB}})^2 + SS_{X1B} + N_B*(\overline{X1_B}-\overline{X1_{AB}})^2 \quad (8)$$

A sum of square of deviation $SS_{X2AB}$ is an integration sum of square of deviation obtained by integrating a sum of square of deviation $SS_{X2A}$ and a sum of square of deviation $SS_{X2B}$ based on the integration average value of the equation (7), and is expressed by the following equation (9).

$$SS_{X2AB} = SS_{X2A} + N_A*(\overline{X2_A}-\overline{X2_{AB}})^2 + SS_{X2B} + N_B*(\overline{X2_B}-\overline{X2_{AB}})^2 \quad (9)$$

The sum of square of deviation $SS_{YAB}$ is the integration sum of square of deviation obtained by integrating the sum of square of deviation $SS_{YA}$ and the sum of square of deviation $SS_{YB}$ based on the integration average value of the equation (2), and is expressed by the equation (4).

A sum of product of deviation $SS_{X1YAB}$ is an integration sum of product of deviation obtained by integrating a sum of product of deviation $SS_{X1YA}$ and a sum of product of deviation $SS_{X1YB}$ based on the integration average values of the equations (6) and (7), and is expressed by the following equation (10).

$$SS_{X1YAB} = SS_{X1YA} + N_A*(\overline{X1_A}-\overline{X1_{AB}})(\overline{Y_A}-\overline{Y_{AB}}) + SS_{X1YB} + N_B*(\overline{X1_B}-\overline{X1_{AB}})(\overline{Y_B}-\overline{Y_{AB}}) \quad (10)$$

A sum of product of deviation $SS_{X2YAB}$ is an integration sum of product of deviation obtained by integrating a sum of product of deviation $SS_{X2YA}$ and a sum of product of deviation $SS_{X2YB}$ based on the integration average values of the equations (6) and (7), and is expressed by the following equation (11).

$$SS_{X1YAB} = SS_{X1YA} + N_A*(\overline{X1_A}-\overline{X1_{AB}})(\overline{Y_A}-\overline{Y_{AB}}) + SS_{X1YB} + N_B*(\overline{X1_B}\times-\overline{X1_{AB}})(\overline{Y_B}-\overline{Y_{AB}}) \quad (11)$$

<Integration Validity Verification Processing (Step S704)>

Figure 10:
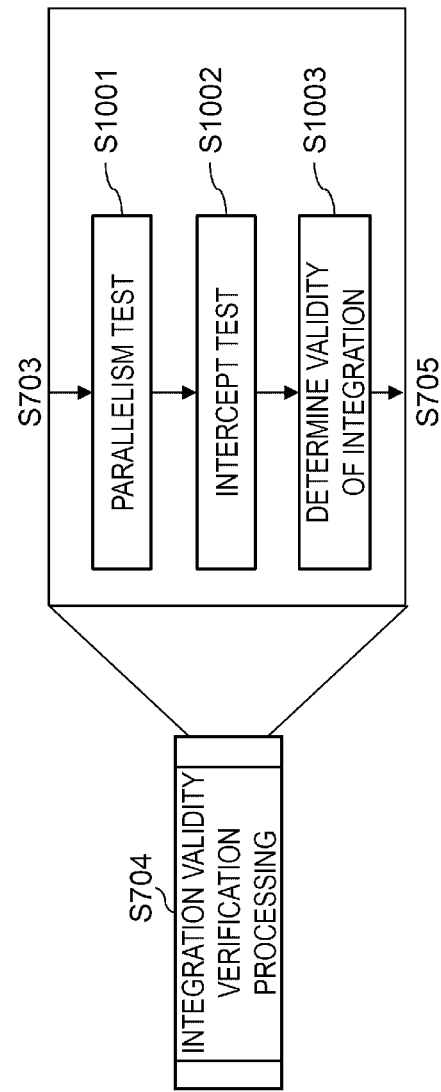
FIG. 10 is a flowchart showing an example of a detailed processing procedure of integration validity verification processing (step S704) performed by the integration device.

FIG. 10 is a flowchart showing an example of a detailed processing procedure of the integration validity verification processing (step S704) by the integration device 101. The integration device 101 executes a parallelism test (step S1001) and an intercept test (step S1002), determines the validity of the integration of the plurality of pieces of statistical information 213 (step S1003), and proceeds to step S705.

The parallelism test (step S1001) is processing of testing a hypothesis that there is a difference in a slope of the regression equation of the integrated statistical information 213. The intercept test (step S1002) is processing of testing a hypothesis that there is a difference in an intercept of the regression equation of the integrated statistical information 213. The determination of the validity of the integration (step S1003) is processing of determining the validity of the integration of the plurality of pieces of statistical information 213 based on a combination of a parallelism test result and an intercept test result. The statistical information integration processing (step S704) will be described by taking the single regression of FIG. 8 as an example.

In the parallelism test (step S1001), the integration device 101 tests a hypothesis that there is a difference between slopes of the two single regression equations indicating the integration models (hereinafter, referred to as pre-integration models) of the two pieces of statistical information 213 to be integrated. Specifically, for example, the integration device 101 calculates a residual sum of squares $\Delta1$ (the following equation (12)) under a hypothesis that the slopes are different and a residual sum of squares $\Delta2$ (the following equation (13)) under a hypothesis that the slopes are the same. Then, the integration device 101 performs the hypothesis test based on an F statistic calculated based on the residual sum of squares $\Delta1$ and the residual sum of squares $\Delta2$.

$$\Delta_1 = \left[SS_{YA} - \frac{(SS_{XYA})^2}{SS_{XA}}\right] + \left[SS_{YB} - \frac{(SS_{XYB})^2}{SS_{XB}}\right] \quad (12)$$

$$\Delta_2 = SS_{YA} + SS_{YB} - \frac{(SS_{XYA}+SS_{XYB})^2}{SS_{XA}+SS_{XB}} \quad (13)$$

For example, the integration device 101 can determine rejection of the hypothesis by using an F value calculated by the following equation (14) and an F distribution with degrees of freedom of 1 and $N_{AB}-4$.

$$F = \left(\frac{\Delta_2}{\Delta_1} - 1\right) \times (N_{AB} - 4) \quad (14)$$

Next, when the hypothesis that the slopes of the two regression equations indicating the two pre-integration models are equal to each other cannot be denied in the parallelism test (step S1001), the integration device 101 tests, in the intercept test (step S1002), the hypothesis that there is a difference between the intercepts of the two regression equations. Specifically, for example, the integration device 101 performs the hypothesis test based on an F statistic calculated based on a residual sum of squares Δ3 (the following equation (15)) under a hypothesis that the two regression equations are on the same straight line.

$$\Delta_3 = SS_Y - \frac{(SS_{XY})^2}{SS_X} \quad (15)$$

For example, the integration device 101 determines rejection of the hypothesis by using an F value calculated by the following equation (16) and an F distribution with degrees of freedom of 1 and $N_{AB}-3$.

$$F = \left(\frac{\Delta_3}{\Delta_1} - 1\right) \times (N_{AB} - 3) \quad (16)$$

In the determination of the validity of the integration (step S1003), the integration device 101 determines that the integration is valid when the hypothesis that the slopes are equal to each other cannot be denied in the parallelism test (step S1001) and the hypothesis that the intercepts are equal to each other cannot be denied in the intercept test (step S1002).

Here, the description has been given using the single regression as an example, and in a case of multiple regression analysis, validity of a post-integration model can be verified by constructing a covariance matrix based on the statistical information and the integration statistical information.

Next, model parameter calculation processing (step S705) will be described in detail. When it is determined in the determination of the validity of the integration (step S1003) that the integration is valid, the integration device 101 calculates a slope a and an intercept b of the integration model as the model parameter 215 by, for example, the following equations (17) and (18).

$$a = \frac{SS_{XY}}{SS_X} \quad (17)$$

$$b = \overline{Y} - a * \overline{X} \quad (18)$$

When it is determined in the determination of the validity of the integration (step S1003) that the integration is not valid, for example, when it is determined that only the slope is common and only the intercept is different, the integration device 101 calculates the common slope by, for example, the following equation (19). Further, the integration device 101 calculates an intercept $b_A$ and an intercept $b_B$ corresponding to each data as the model parameter by, for example, the following equations (20) and (21).

$$a = \frac{SS_{XYA} + SS_{XYB}}{SS_{XA} + SS_{XB}} \quad (19)$$

$$b_A = \overline{Y}_A - a * \overline{X}_A \quad (20)$$

$$b_B = \overline{Y}_B - a * \overline{X}_B \quad (21)$$

Here, the description has been given using the single regression as an example, and in the case of the multiple regression analysis, the model parameter of the integration model can be calculated by constructing a covariance matrix based on the statistical information 213 and the integration statistical information 214.

<Display Screen>

Figure 11:
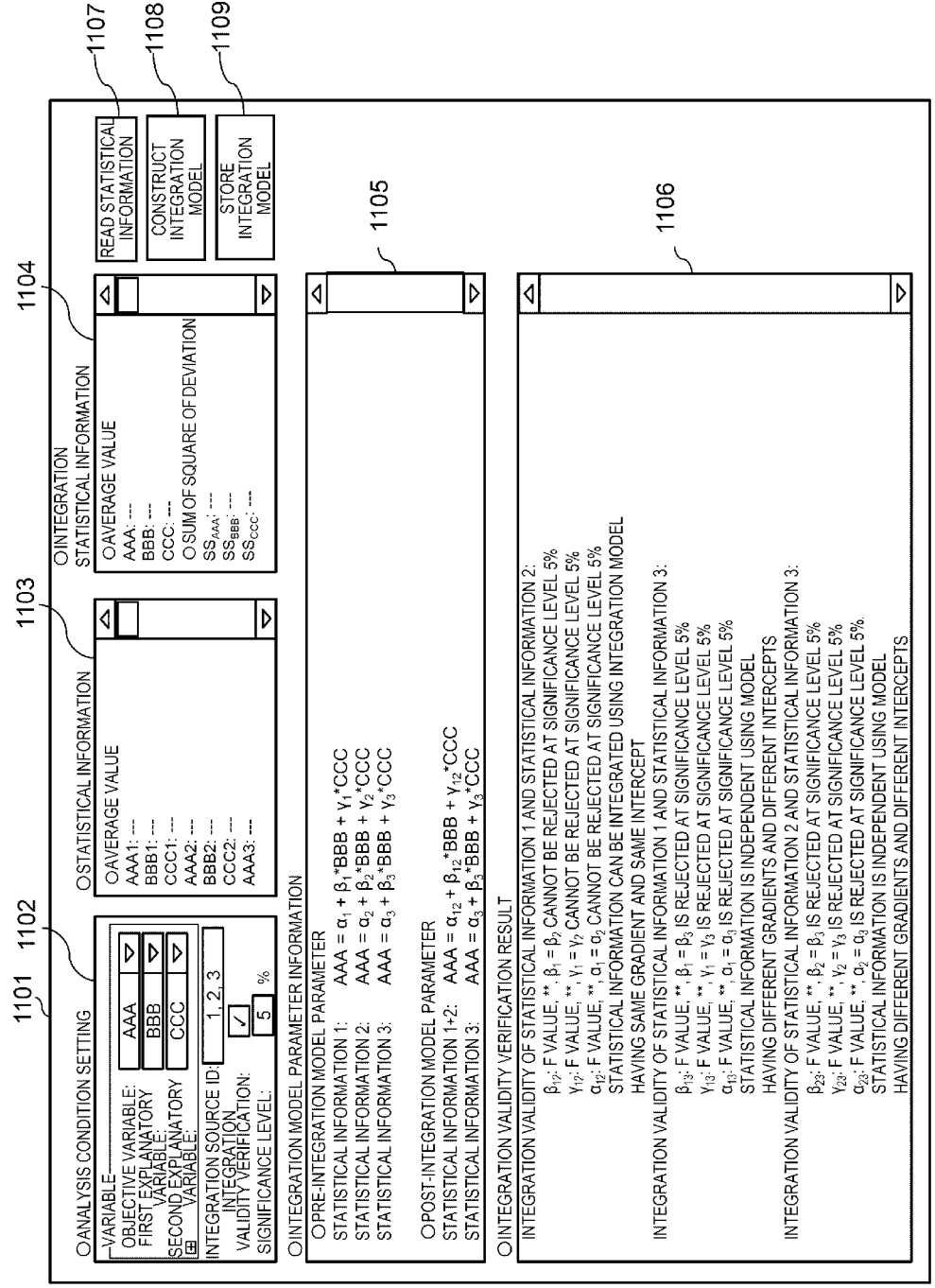
FIG. 11 is a diagram showing an example of a display screen of the integration device.

FIG. 11 is a diagram showing an example of a display screen of the integration device 101. A display screen 1101 is displayed on a display that is the output device 204 of the integration device 101. The display screen 1101 includes an analysis condition setting area 1102, a statistical information display area 1103, an integration statistical information display area 1104, an integration model parameter information display area 1105, an integration validity verification result display area 1106, a statistical information read button 1107, an integration model construction button 1108, and an integration model storage button 1109.

The analysis condition setting area 1102 is an area for setting the analysis condition 212. In the analysis condition setting area 1102, in step S701, in addition to the objective variable, the first explanatory variable, and the second explanatory variable in the variable information table 401 and the integration source ID in the integration source information table 402, the integration validity verification can be designated by a check box, and a significance level when the integration validity verification is performed can also be designated.

The statistical information display area 1103 is an area for displaying the statistical information 213. Specifically, for example, when detecting pressing of the statistical information read button 1107 by an user, the integration device 101 reads the statistical information 213 from the statistical information DB 102 (step S702), and displays the statistical information 213 in the statistical information display area 1103.

The integration statistical information display area 1104 is an area for displaying the integration statistical information 214. Specifically, for example, when detecting the pressing of the statistical information read button 1107 by the user, the integration device 101 calculates an integration statistical information tail using the statistical information 213 designated by the integration source ID in the analysis condition setting area 1102 among the statistical information 213 read from the statistical information DB 102 (step S703), and displays the integration statistical information 214 (800AB, 900AB) as a calculation result in the integration statistical information display area 1104.

The integration model parameter information display area 1105 is an area for displaying the pre-integration and post-integration model parameters. Specifically, for example, when detecting pressing of the integration model construction button 1108, the integration device 101 executes the integration model parameter calculation processing on the integration statistical information determined to be valid by the integration validity verification processing (step S704) to calculate the model parameter 215 (step S705), and displays the model parameter 215, which is the calculation result, in the integration model parameter information display area 1105 together with the model parameter 215 before the integration.

For example, in the integration model parameter information display area 1105, the model parameters 215 of the integration statistical information 214 obtained by integrating the "statistical information 1" and the "statistical information 2" are an intercept $\alpha_{12}$, a slope $\beta_{12}$, and a slope $\gamma_{12}$. Further, model parameters of the "statistical information 3" that is not integrated with the "statistical information 1" and the "statistical information 2" are an intercept $\alpha_3$, a slope $\beta_3$, and a slope $\gamma_3$.

The integration validity verification result display area 1106 is an area for displaying an integration validity verification result by the integration validity verification processing (step S704). Specifically, for example, in the integration validity verification result display area 1106, the integration validity verification result for a combination of two pieces of statistical information designated by the integration source ID is displayed. More specifically, the integration device 101 calculates the F value for the intercept and the slope of each combination of the statistical information, and determines whether the intercept and the slope can be rejected with the significance level set in the analysis condition 212. When the intercept and the slope cannot be rejected, the integration device 101 displays a verification result indicating that the statistical information can be integrated using the integration model having the same gradient and the same intercept. On the other hand, when the intercept and the slope can be rejected, the integration device 101 displays a verification result indicating that the statistical information is independent using the integration model as an integration model having different gradients and different intercepts.

When the integration model storage button 1109 is pressed, the integration device 101 stores the model parameter 215 of the integration statistical information 214 in the integration model DB 103.

In the embodiment described above, in the integration source information table 402, the integration source ID is the identification information i for uniquely specifying the private environment PEi. However, the integration source ID may be the identification information for uniquely specifying data indicating a part of items of the private data 220 in the private environment PEi.

Further, the integration device 101 may select a feature amount of machine learning based on the verification result of the integration validity verification processing (step S704). Specifically, for example, when the hypothesis is not rejected in the parallelism test (step S1001), the integration device 101 selects the explanatory variable corresponding to the slope as the feature amount of a machine learning model. For example, in the integration model (AAA=$\alpha_{12}$+$\beta_{12}$×BBB+$\gamma_{12}$×CCC) of the "statistical information 1+2" in the integration model parameter information display area 1105 of FIG. 11, $\beta_{12}$ and $\gamma_{12}$ are unrejected slopes, BBB is an explanatory variable corresponding to the slope $\beta_{12}$, and CCC is an explanatory variable corresponding to the slope $\gamma_{12}$. Therefore, BBB and CCC are selected as feature amounts (hereinafter referred to as effective feature amounts) of the machine learning model. In addition, AAA on a left side of the integration model is selected as correct answer data of the machine learning model. A combination of the effective feature amounts and the correct answer data is a learning data set for generating the machine learning model.

In a statistical model (AAA=$\alpha_3$+$\beta_3$×BBB+$\gamma_3$×CCC) of the unintegrated "statistical information 3", when the hypothesis is not rejected in the parallelism test (step S1001), $\beta_3$ and $\gamma_3$ are the unrejected slopes, BBB is an explanatory variable corresponding to the slope $\beta_3$, and CCC is an explanatory variable corresponding to the slope $\gamma_3$. Therefore, BBB and CCC are selected as the effective feature amounts of the machine learning model, and AAA on a left side of the model is selected as the correct answer data of the machine learning model.

Further, the integration device 101 creates values (obtained based on the integration statistical information 214 and the statistical information 213) of the selected feature amounts BBB and CCC as learning data, and creates the learning data set by combining the learning data and prediction data output when the learning data is given to the integration model. Then, the integration device 101 generates the machine learning model using the learning data set, and transmits a parameter of the generated machine learning model to each private data analysis device PSi.

The private data analysis device PSi creates the machine learning model using the parameter of the machine learning model. The private data analysis device PSi inputs the private data 220 corresponding to the selected feature amount to the machine learning model and outputs a prediction result. Then, the private data analysis device PSi calculates a difference between the prediction result and a value of the actual objective variable, and transmits the difference to the integration device 101. The integration device 101 updates the machine learning model by error back propagation using the difference.

In this way, by constructing the machine learning model that can be sequentially corrected based on the integration model or the statistical model, prediction accuracy can be improved.

Further, the private data analysis device PSi determines a deviation between the private data 220 and the statistical information 213 based on a magnitude of a difference (for example, Euclidean distance) between the private data 220 and the statistical information 213. When the magnitude of the difference is equal to or larger than a threshold, the private data analysis device PSi recalculates the statistical information 213 with the latest private data 220 including data whose date and time is newer than a date and time of the previous private data 220.

The latest private data 220 may or may not include the previous private data 220. For example, when the private data 220 is present for each year, the private data analysis device PSi may recalculate the statistical information 213 only with the private data 220 of a latest year. Further, the private data analysis device PSi may recalculate the statistical information 213 with the private data 220 of past five years including the latest year. In this case, the private data analysis device PSi previously calculates the statistical information 213 using the private data 220 for five years from six years ago to one year ago, and this time, the private data analysis device PSi calculates the statistical information 213 using the private data 220 for five years from five years ago to this year.

The private data analysis device PSi transmits the recalculated statistical information 213 to the integration device 101. The integration device 101 executes the integration model construction processing shown in FIG. 7 in response to the reception of the statistical information 213. Accordingly, the integration model is updated.

Further, for each item of the private data 220 included in each private data analysis device PSi, the items may be semantically identical and notations of item names may be different between the private data analysis devices PSi (for example, "body length" and "height"). In such a case, the integration device 101 may have an item master table for absorbing the difference in the item name for each private data analysis device PSi.

The item master table is a table in which a conversion destination item name and the item name (conversion source item name) of the private data 220 are associated with each other. For example, when the private data analysis device PS1 describes one item "body length" of the private data 220 as "back height", an item master table for the private data analysis device PS1 has information in which the conversion destination item name "body length" and the conversion source item name "back height" are associated with each other.

Further, when another private data analysis device PS2 describes one item "body length" of the private data 220 as "height", an item master table for the private data analysis device PS2 has information in which the conversion destination item name "body length" and the conversion source item name "height" are associated with each other.

When the integration device 101 executes the integration model construction processing shown in FIG. 7, the item "back height" of the statistical information 213 from the private data analysis device PS1 matches the conversion source item name "back height" of the item master table for the private data analysis device PS1. Therefore, the integration device 101 converts the item "back height" of the statistical information 213 into the item "body length" by the item master table for the private data analysis device PS1.

The item "height" of the statistical information 213 from the private data analysis device PS2 matches the conversion source item name "height" of the item master table for the private data analysis device PS2. Therefore, the integration device 101 converts the item "height" into the item "body length" by the item master table for the private data analysis device PS2. Accordingly, even when the notation of the item name of the same item is different between the private data analysis devices PSi, the statistical information 213 from the private data analysis device PS1 and the statistical information 213 from the private data analysis device PS2 can be integrated.

In this way, according to the integration device 101 of the present embodiment, the integration statistical information 214 obtained by integrating the statistical information 213 between the private data analysis devices PSi can be generated without accessing the private data 220 included in the private data analysis device PSi.

Further, the integration device 101 according to the embodiment described above may be configured as in the following (1) to (13).

(1) The integration device 101 includes the processor 201 that executes a program and the storage device 202 that stores the program, and is accessible to the statistical information 213 based on the private data 220 of each of the plurality of private data analysis devices PSi. The processor 201 executes: acquisition processing (step S702) of acquiring first statistical information and second statistical information from the plurality of pieces of statistical information 213; integration processing (step S703) of integrating the first statistical information and the second statistical information acquired by the acquisition processing by statistical processing based on the number of first data of first analysis target data used for statistical processing of the first statistical information and the number of second data of second analysis target data used for statistical processing of the second statistical information; and output processing (step S706) of outputting the integration statistical information 214 obtained by the integration processing.

Accordingly, the integration device 101 can integrate the first statistical information and the second statistical information without accessing the private data 220. Therefore, leakage of the private data 220 is prevented.

(2) In the integration device 101 of the above-described (1), in the acquisition processing, the processor 201 acquires third statistical information from the plurality of pieces of statistical information and acquires the integration statistical information as fourth statistical information, and in the integration processing, the processor integrates the third statistical information and the fourth statistical information acquired by the acquisition processing by statistical processing based on the number of first data of third analysis target data used for statistical processing of the third statistical information and a sum of the number of first data and the number of second data used for statistical processing of the fourth statistical information.

Accordingly, the integration of the first to third statistical information can be tried.

(3) In the integration device 101 of the above-described (1), the processor 201 executes generation processing (step S705) of generating, using the integration statistical information 214, the integration model for predicting the value of the objective variable in first private data 220 and second private data 220 based on the value of one or more explanatory variables in the first private data 220 and the second private data 220.

(4) In the integration device 101 of the above-described (1), the processor 201 executes verification processing (step S704) of verifying validity of the integration of the first statistical information and the second statistical information in the integration processing, and in the output processing, the processor 201 outputs the verification result of the verification processing.

Accordingly, the user of the integration device 101 can confirm the validity of the integration.

(5) In the integration device 101 of the above-described (3), the processor 201 executes the verification processing of verifying validity of the integration of the first statistical information and the second statistical information in the integration processing, and in the generation processing, the processor 201 generates the integration model using the integration statistical information based on the verification result of the verification processing.

Accordingly, the integration device 101 can calculate a predicted value of the objective variable in the private data 220 without accessing the private data 220.

(6) In the integration device 101 of the above-described (5), in the verification processing, the processor 201 executes a statistical test of a hypothesis that a coefficient (slope and intercept) of a first statistical model related to the first statistical information is equal to a coefficient (slope and intercept) of a second statistical model related to the second statistical information, and verifies the validity of the integration of the first statistical information and the second statistical information based on a test result.

Accordingly, the validity of the integration can be statistically guaranteed.

(7) In the integration device 101 of the above-described (6), in the verification processing, the processor 201 executes a statistical test for testing a hypothesis that a slope of the first statistical model is equal to a slope of the second statistical model and a statistical test for testing a hypothesis that an intercept of the first statistical model is equal to an intercept of the second statistical model, when both the hypothesis that the slopes are equal and the hypothesis that the intercepts are equal cannot be denied, the integration is determined to be valid, when the hypothesis that the slopes are equal cannot be denied and the hypothesis that the intercepts are equal is denied, the first statistical model and the second statistical model are determined to be independent models having the equal slopes and different intercepts, and when the hypothesis that the slopes are equal is denied, the integration is determined to be not valid.

Accordingly, the validity of the integration can be divided into temporary tests of the slope and the intercept, and can be specifically executed.

(8) The integration device 101 of the above-described (1) is accessible to each of the analysis target devices, and in the acquisition processing, the processor 201 acquires the first statistical information and the second statistical information from the plurality of pieces of statistical information 213 included in the plurality of private data analysis devices PSi.

Accordingly, the integration device 101 can directly acquire the statistical information 213 from the private data analysis device PSi.

(9) The integration device 101 of the above-described (1) is accessible to a statistical information DB 102 that stores the plurality of pieces of statistical information 213, and in the acquisition processing, the processor 201 acquires the first statistical information and the second statistical information from the statistical information DB 102.

Accordingly, the integration device 101 can acquire the statistical information 213 even when the integration device 101 cannot access the private data analysis device PSi.

(10) In the integration device 101 of the above-described (1), in the acquisition processing, the processor 201 acquires the first statistical information and the second statistical information from the plurality of pieces of statistical information based on the private data 220 including a value indicating item information indicating a calculation target as a result of transmitting the item information to the private data analysis device.

(11) In the integration device 101 of the above-described (3), the processor 201 executes setting processing (step S701) of setting the one or more explanatory variables and the objective variable, in the acquisition processing, the processor 201 acquires the first statistical information and the second statistical information from the plurality of pieces of statistical information 213 based on the private data 220 including the values indicating the one or more explanatory variables and the objective variable, and in the generation processing, the processor 201 generates the integration model for predicting the value of the objective variable based on the value of the one or more explanatory variables.

Accordingly, the integration device 101 can narrow down the explanatory variable and the objective variable as the analysis condition to generate the integration model.

(12) In the integration device 101 of the above-described (3), the processor 201 executes verification processing of verifying validity of the integration of the first statistical information and the second statistical information in the integration processing, and in the generation processing, based on a verification result of the verification processing, the processor 201 generates a machine learning model for predicting the value of the objective variable by taking the one or more explanatory variables as a feature amount.

Accordingly, the integration model and the statistical model (regression equations that is not integrated) can be integrated into one machine learning model. Further, the integration device 101 transmits the machine learning model to the private data analysis device PSi, and the private data analysis device PSi inputs the private data 220 to the machine learning model to calculate the predicted value of the objective variable, calculates the difference between the predicted value and the value of the objective variable, and returns the difference to the integration device 101. Accordingly, the integration device 101 can update the machine learning model using the difference without accessing the private data 220.

(13) The integration device 101 of the above-described (1) includes a table in which a conversion source item name is associated with a conversion destination item name, in the acquisition processing, when an item name of a variable in the statistical information matches the conversion source item name, the processor 201 converts the item name of the variable in the statistical information into the conversion destination item name, and in the integration processing, the processor 201 integrates the first statistical information and the second statistical information based on a conversion result of the item name.

Accordingly, since the difference between the item names is absorbed, integration in which variables of semantically identical items are treated as separate variables can be reduced.

The invention is not limited to the embodiment described above, and includes various modifications and equivalent configurations within the scope of the appended claims. For example, the embodiment described above has been described in detail in order to make the invention easy to understand, and the invention is not necessarily limited to those which have all the described configurations. A part of a configuration of a certain embodiment may be replaced with a configuration of another embodiment. The configuration of another embodiment may be added to the configuration of the certain embodiment. Further, a part of the configuration of an embodiment may be added to, deleted from, or replaced with another configuration.

Further, a part or all of the configurations, functions, processing units, processing methods described above and the like may be implemented by hardware, for example, by designing with an integrated circuit, or may be implemented by software, with the processor 201 to interpret and execute a program for implementing each function.

Information such as a program, a table, and a file for implementing each function can be stored in a storage device such as a memory, a hard disk, and a solid state drive (SSD), or a recording medium such as an integrated circuit (IC) card, a SD card, and a digital versatile disc (DVD).

Control lines and information lines indicate what is considered necessary for description, and not all control lines or information lines in a product are shown. In practice, it may be considered that almost all the configurations are connected with each other.

What is claimed is:

1. An integration device accessible to statistical information based on analysis target data of each of a plurality of analysis target devices, the integration device comprising:
a processor configured to execute a program; and
a storage device configured to store the program, wherein the processor is configured to execute
acquisition processing of acquiring first statistical information from a first target device and second statistical information from a second target device, the first and second target devices comprising a plurality of pieces of statistical information,
integration processing of integrating the first statistical information and the second statistical information acquired by the acquisition processing by statistical processing based on a number of first data of first analysis target data used for statistical processing of the first statistical information and a number of second data of second analysis target data used for statistical processing of the second statistical information, and output processing of outputting integration statistical information obtained by the integration processing;

wherein the processor executes generation processing of generating, using the integration statistical information, an integration model for predicting a value of an objective variable in the first analysis target data and the second analysis target data based on a value of one or more explanatory variables in the first analysis target data and the second analysis target data; wherein in the generation processing, the processor generates the integration model using the integration statistical information based on a verification result of the verification processing; wherein in the verification processing, the processor executes a statistical test of a hypothesis that a coefficient of a first statistical model related to the first statistical information is equal to a coefficient of a second statistical model related to the second statistical information, and verifies the validity of the integration of the first statistical information and the second statistical information based on a test result;

wherein in the verification processing, the processor executes a statistical test for testing a hypothesis that a slope of the first statistical model is equal to a slope of the second statistical model and a statistical test for testing a hypothesis that an intercept of the first statistical model is equal to an intercept of the second statistical model, when both the hypothesis that the slopes are equal and the hypothesis that the intercepts are equal cannot be denied, the integration is determined to be valid, when the hypothesis that the slopes are equal cannot be denied and the hypothesis that the intercepts are equal is denied, the first statistical model and the second statistical model are determined to be independent models having the equal slopes and different intercepts, and when the hypothesis that the slopes are equal is denied, the integration is determined to be not valid, wherein the processor executes verification processing of verifying validity of the integration of the first statistical information and the second statistical information in the integration processing, and wherein in the output processing, the processor outputs a verification result of the verification processing.

2. The integration device according to claim 1, wherein in the acquisition processing, the processor acquires third statistical information from the plurality of pieces of statistical information and acquires the integration statistical information as fourth statistical information, and in the integration processing, the processor integrates the third statistical information and the fourth statistical information acquired by the acquisition processing by statistical processing based on the number of first data of third analysis target data used for statistical processing of the third statistical information and a sum of the number of first data and the number of second data used for statistical processing of the fourth statistical information.

3. The integration device according to claim 1, wherein the processor executes setting processing of setting the one or more explanatory variables and the objective variable, in the acquisition processing, the processor acquires the first statistical information and the second statistical information from the plurality of pieces of statistical information based on the analysis target data including values indicating the one or more explanatory variables and the objective variable, and in the generation processing, the processor generates the integration model for predicting the value of the objective variable based on the value of the one or more explanatory variables.

4. The integration device according to claim 1, wherein the processor executes verification processing of verifying validity of the integration of the first statistical information and the second statistical information in the integration processing, and in the generation processing, based on a verification result of the verification processing, the processor generates a machine learning model for predicting the value of the objective variable by taking the one or more explanatory variables as a feature amount.

5. The integration device according to claim 1, wherein the integration device is accessible to each of the analysis target devices, and in the acquisition processing, the processor acquires the first statistical information and the second statistical information from the plurality of pieces of statistical information of the plurality of analysis target devices.

6. The integration device according to claim 1, wherein the integration device is accessible to a statistical information database that stores the plurality of pieces of statistical information, and in the acquisition processing, the processor acquires the first statistical information and the second statistical information from the statistical information database.

7. The integration device according to claim 1, wherein in the acquisition processing, the processor acquires the first statistical information and the second statistical information from the plurality of pieces of statistical information based on the analysis target data including a value indicating item information indicating a calculation target as a result of transmitting the item information to the analysis target device.

8. The integration device according to claim 1, further comprising:

a table in which a conversion source item name is associated with a conversion destination item name, wherein in the acquisition processing, when an item name of a variable in the statistical information matches the conversion source item name, the processor converts the item name of the variable in the statistical information into the conversion destination item name, and in the integration processing, the processor integrates the first statistical information and the second statistical information based on a conversion result of the item name.

9. An integration method executed by an integration device, the integration device including a processor that executes a program and a storage device that stores the program, the integration device being accessible to statistical information based on analysis target data of each of a plurality of analysis target devices, the integration method comprising:

acquisition processing, executed by the processor, of acquiring first statistical information from a first target device and second statistical information from a second target device, the first and second target devices comprising a plurality of pieces of statistical information;

integration processing, executed by the processor, of integrating the first statistical information and the second statistical information acquired by the acquisition processing by statistical processing based on the number of first data of first analysis target data used for statistical processing of the first statistical information and the number of second data of second analysis target data used for statistical processing of the second statistical information;

output processing, executed by the processor, of outputting integration statistical information obtained by the integration processing;

generation processing, executed by the processor, of generating, using the integration statistical information, an integration model for predicting a value of an objective variable in the first analysis target data and the second analysis target data based on a value of one or more explanatory variables in the first analysis target data and the second analysis target data;

verification processing, executed by the processor, of verifying validity of the integration of the first statistical information and the second statistical information in the integration processing, wherein in the generation processing, the processor generates the integration model using the integration statistical information based on a verification result of the verification processing; wherein in the verification processing, the processor executes a statistical test of a hypothesis that a coefficient of a first statistical model related to the first statistical information is equal to a coefficient of a second statistical model related to the second statistical information, and verifies the validity of the integration of the first statistical information and the second statistical information based on a test result;

and wherein in the verification processing, the processor executes a statistical test for testing a hypothesis that a slope of the first statistical model is equal to a slope of the second statistical model and a statistical test for testing a hypothesis that an intercept of the first statistical model is equal to an intercept of the second statistical model, when both the hypothesis that the slopes are equal and the hypothesis that the intercepts are equal cannot be denied, the integration is determined to be valid, when the hypothesis that the slopes are equal cannot be denied and the hypothesis that the intercepts are equal is denied, the first statistical model and the second statistical model are determined to be independent models having the equal slopes and different intercepts, and when the hypothesis that the slopes are equal is denied, the integration is determined to be not valid.

10. A non-transitory computer readable storage medium comprising an integration program stored thereon, and configured to cause a processor accessible to statistical information based on analysis target data of each of a plurality of analysis target devices to execute:

acquisition processing of acquiring first statistical information and second statistical information from a plurality of pieces of statistical information;

integration processing of integrating the first statistical information and the second statistical information acquired by the acquisition processing by statistical processing based on the number of first data of first analysis target data used for statistical processing of the first statistical information and the number of second data of second analysis target data used for statistical processing of the second statistical information; and output processing of outputting integration statistical information obtained by the integration processing;

generation processing, of generating, using the integration statistical information, an integration model for predicting a value of an objective variable in the first analysis target data and the second analysis target data based on a value of one or more explanatory variables in the first analysis target data and the second analysis target data; and verification processing, executed by the processor, of verifying validity of the integration of the first statistical information and the second statistical information in the integration processing, wherein in the generation processing, the processor generates the integration model using the integration statistical information based on a verification result of the verification processing; wherein in the verification processing, the processor executes a statistical test of a hypothesis that a coefficient of a first statistical model related to the first statistical information is equal to a coefficient of a second statistical model related to the second statistical information, and verifies the validity of the integration of the first statistical information and the second statistical information based on a test result;

and wherein in the verification processing, the processor executes a statistical test for testing a hypothesis that a slope of the first statistical model is equal to a slope of the second statistical model and a statistical test for testing a hypothesis that an intercept of the first statistical model is equal to an intercept of the second statistical model, when both the hypothesis that the slopes are equal and the hypothesis that the intercepts are equal cannot be denied, the integration is determined to be valid, when the hypothesis that the slopes are equal cannot be denied and the hypothesis that the intercepts are equal is denied, the first statistical model and the second statistical model are determined to be independent models having the equal slopes and different intercepts, and when the hypothesis that the slopes are equal is denied, the integration is determined to be not valid.

11. An integration device accessible to statistical information based on analysis target data of each of a plurality of analysis target devices, the integration device comprising:

a processor configured to execute a program; and a storage device configured to store the program, wherein the processor is configured to execute acquisition processing of acquiring first statistical information from a first target device and second statistical information from a second target device, the first and second target devices comprising a plurality of pieces of statistical information, integration processing of integrating the first statistical information and the second statistical information acquired by the acquisition processing by statistical processing based on a number of first data of first analysis target data used for statistical processing of the first statistical information and a number of second data of second analysis target data used for statistical processing of the second statistical information, and output processing of outputting integration statistical information obtained by the integration processing;

wherein the processor executes generation processing of generating, using the integration statistical information, an integration model for predicting a value of an objective variable in the first analysis target data and the second analysis target data based on a value of one or more explanatory variables in the first analysis target data and the second analysis target data; wherein the processor executes verification processing of verifying validity of the integration of the first statistical information and the second statistical information in the integration processing, and in the generation processing, the processor generates the integration model using the integration statistical information based on a verification result of the verification processing; wherein in the verification processing, the processor executes a statistical test of a hypothesis that a coefficient of a first statistical model related to the first statistical information is equal to a coefficient of a second statistical model related to the second statistical information, and verifies the validity of the integration of the first statistical information and the second statistical information based on a test result;

and wherein in the verification processing, the processor executes a statistical test for testing a hypothesis that a slope of the first statistical model is equal to a slope of the second statistical model and a statistical test for testing a hypothesis that an intercept of the first statistical model is equal to an intercept of the second statistical model, when both the hypothesis that the slopes are equal and the hypothesis that the intercepts are equal cannot be denied, the integration is determined to be valid, when the hypothesis that the slopes are equal cannot be denied and the hypothesis that the intercepts are equal is denied, the first statistical model and the second statistical model are determined to be independent models having the equal slopes and different intercepts, and when the hypothesis that the slopes are equal is denied, the integration is determined to be not valid.

* * * * *